United States Patent [19]
Smith et al.

[11] Patent Number: 5,731,451
[45] Date of Patent: Mar. 24, 1998

[54] MODIFIED POLYALKYLAUMINOXANE COMPOSITION FORMED USING REAGENT CONTAINING ALUMINUM TRIALKYL SILOXIDE

[75] Inventors: Gregory M. Smith, Danbury, Conn.; Dennis B. Malpass, La Porte, Tex.; Stanley W. Palmaka, Yonkers, N.Y.

[73] Assignee: Akzo Nobel NV, Arnhem, Netherlands

[21] Appl. No.: 679,028

[22] Filed: Jul. 12, 1996

[51] Int. Cl.$^6$ .................. C07F 5/06; B01J 31/00
[52] U.S. Cl. .................. 556/173; 556/175; 556/187; 556/189; 502/104; 502/103; 502/107; 502/117; 526/160; 526/943
[58] Field of Search .................. 556/187, 189, 556/175, 181, 173; 502/104, 107, 103, 117; 526/160, 943

[56] References Cited

U.S. PATENT DOCUMENTS

| | | | |
|---|---|---|---|
| 3,629,216 | 12/1971 | Iwasaki et al. | 260/88.2 |
| 3,969,332 | 7/1976 | Gloriod et al. | 526/128 |
| 5,329,032 | 7/1994 | Tran et al. | 556/179 |
| 5,332,706 | 7/1994 | Nowlin et al. | 502/107 |
| 5,391,529 | 2/1995 | Sangokoya et al. | 502/103 |

OTHER PUBLICATIONS

C.C. Landry et al., "Siloxy-Substituted Alumoxanes: Synthesis from Polydialkylsiloxanes and Trimethylaluminum, and Application as Aluminosilicate Precursors", J. Mater. Chem., 1993, 3(6), 597–602.

A.W. Apbleet et al., "Synthesis and Characterization of Triethylsiloxy-Substituted Alumoxanes: Their Structural Relationship to the Minerals Boehmite and Diaspore", Chem. Mater. 1992, 4, 167–182.

*Primary Examiner*—Porfirio Nazario-Gonzalez
*Attorney, Agent, or Firm*—Richard P. Fennelly; Louis A. Morris

[57] ABSTRACT

A process is disclosed for forming an aluminoxane composition comprising methylaluminoxane by mixing trimethylaluminum, or a mixture of trimethylaluminum and one or more other trihydrocarbylaluminum compounds, with an organoaluminum compound containing a trialkylsiloxide moiety and then oxygenating the mixture to form the aluminoxane. Oxygenation can be carried out by controlled hydrolysis or by treatment with an organic compound containing carbon-oxygen bonds, such as carbon dioxide. A preferred trialkylsiloxide moiety is of the formula —OSi$(CH_3)_3$, such as in a compound of the formula $(CH_3)_2AlOSi(CH_3)_3$.

21 Claims, No Drawings

MODIFIED POLYALKYLALUMINOXANE COMPOSITION FORMED USING REAGENT CONTAINING ALUMINUM TRIALKYL SILOXIDE

BACKGROUND OF THE INVENTION

The present invention relates to a novel synthesis of aluminoxanes. Aluminoxanes are well known as components for olefin polymerization catalysts.

Aluminoxane compounds are chemical species that incorporate Al—O—Al moieties. While a wide range of aluminoxane species are known their exact structures are not precisely known. The following structures (where R is alkyl and X is an integer of from about 1 to about 40) have been depicted:

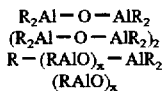

Cyclic and cage cluster structures have also been proposed. Such materials, as would be recognized by the person of ordinary skill in the art are complex mixtures of various species which can easily undergo dynamic exchange reactions and structural rearrangements. A recent review of these materials was authored by S. Pasynkiewicz and appears in Polyhedron, Vol. 9, pp. 429–453 (1990).

Polymethylaluminoxanes (PMAOs), for example, are well known materials with wide utility in olefin polymerization using single-site, or metallocene-based, polymerization catalyst systems (See, for example, Col. 1, lines 14–29 of U.S. Pat. No. 4,960,878 to C. C. Crapo et al.). PMAOs are prepared by controlled hydrolysis of trimethylaluminum (TMAL). Since TMAL is an expensive starting material, the resulting PMAO is expensive. Generally, hydrolysis occurs with some loss of aluminum to insoluble species. Generally, PMAOs also have very low solubility in aliphatic solvents, which limits their utility, as well as poor storage stability for solutions containing them. (See, for example, Col. 1, lines 30–46 of U.S. Pat. No. 4,960,878). Finally, it is generally polymethylaluminoxanes that have been the most useful products of this general class of material: other alkylaluminoxanes do not work as well.

The problems of low yield, poor solubility, poor storage stability, and expensive reagents in preparation of PMAO have previously been attacked, with only limited success, in several ways. One method was to make predominantly PMAO, but include some components from hydrolysis of other aluminum alkyls, to form the so-called "modified methylaluminoxane" (MMAO). This yields predominantly methyl-containing aluminoxanes in improved yields, with improved solution storage stability as well as improved solubility in aliphatic solvents, at lower cost. However, since alkyl groups other than methyl are present, these materials are not always as effective as conventional PMAO.

The prior art contains certain disclosures germane to the composition derived from the instant invention. For example, U.S. Pat. No. 5,329,032 to N. H. Tran illustrates, in Col. 7, the addition of triethylsilanol, as a solution stabilizer additive, at 1 mole %, to a toluene solution containing PMAO, with a generic description of using such solution stabilizer additives at from 0.1 mole % to 10 mole % (at Col. 3, lines 25–27). The composition formed by such processes would form trialkylsiloxide ($R_3SiO$—Al) moieties in the aluminoxanes. Also relevant to the composition of the instant invention is European Patent Application 621 279 (issued in the US as U.S. Pat. No. 5,391,529), to S. A. Sangokoya, which discloses the treatment of aluminoxanes with alkyldisiloxanes to form siloxy aluminum compounds. The aforementioned patent, U.S. Pat. No. 5,329,032, teaches that solution stabilizer additives can be introduced "(1) by originally reacting and/or complexing trimethylaluminum, the compound containing the electron rich heteroatom and the selected hydrocarbyl moiety or moieties, and water as reagents; or (2) by combining . . . with a pre-formed aluminoxane" (Col. 2, line 2).

None of these disclosures address the problem of improving the yield of soluble aluminoxane.

SUMMARY OF THE INVENTION

The present invention, in one embodiment, relates to a process for forming a composition comprising oligomeric alkylaluminoxane and moieties having the structure —$OSiR_3$, where R, which can be the same or different, is hydrocarbyl, such as lower alkyl, such as methyl. This process comprises initially treating a composition comprising trialkylaluminum with a reagent containing an aluminum trialkyl siloxide moiety, such as dimethyl aluminum trimethyl siloxide, followed by oxygenation.

Oxygenation of trialkylaluminum compositions has often been accomplished by the addition of water in some form. Copending U.S. Ser. No. 08/576,892, filed Dec. 22, 1995 shows that oxygenation can also be accomplished using a non-hydrolytic process. In regard to the present invention, oxygenation should therefore be construed as covering any method for introducing the aluminoxane moieties into the desired composition.

DESCRIPTION OF PREFERRED EMBODIMENTS

While broader aspects of the process of the present invention relate to use of a trialkylaluminum reagent or even triaryl or alkyl-aryl aluminum reagents, it is preferred to utilize trimethylaluminum as the organoaluminum compound in such a process. Hence, the remaining discussion will focus on such a preferred embodiment, although it is to be understood that the process claims contained herein are not so limited.

As just mentioned, a preferred embodiment of the present invention relates to a process for forming a composition comprising oligomeric methylaluminoxane and moieties having the structure Al—$OSi(R)_3$, where R is methyl or a mixture of methyl and hydrocarbyl, which comprises initially treating a composition comprising trimethylaluminum, in an appropriate organic solvent (aliphatic and/or aromatic, as known to the person of ordinary skill in the art), or in the absence of solvent, with a reagent containing the Al—O—$SiR_3$ moiety, followed by oxygenation to ultimately form a composition comprising oligomeric methylaluminoxane and moieties having the structure $AlOSi(R)_3$, as earlier defined.

The present invention is most useful where an improved composition or process for a methylaluminoxane is needed, and the methylaluminum portion of the composition must remain relatively unmodified. The invention leaves the methylaluminum component (derived from the TMAL reagent) relatively unmodified, unless a higher alkyl group-containing hydrocarbylaluminum reagent is also used.

Once some aluminum trialkyl siloxide is introduced, for example, by treatment of TMAL with dimethylaluminum trimethylsiloxide (DMAL-S), this intermediate composition can be further oxygenated (forming additional aluminoxane). Because of the prior introduction of trialkyl siloxide moieties, the amount of water required for hydrolysis to catalytically useful aluminoxane compositions is reduced. This results in improved recovery of soluble aluminum, while still yielding good polymerization activity.

Other advantages of this invention include improved solubility, or storage stability, or both, for the aluminoxane product formed.

If desired, supported polyalkylaluminoxane compositions can be prepared by conducting the aforementioned reaction in the presence of a suitable support material. Alternatively, supported alkylaluminoxanes may also be prepared by forming the alkylaluminoxanes of this invention in a discrete, separate step and subsequently allowing the alkylaluminoxane to react with the support material. Oxidic support materials, such as silica, are especially preferred.

As will be appreciated by the person of ordinary skill in the art, the aluminoxane products that can be made by the process of the present invention are useful as cocatalysts in those single-site (metallocene-based) catalyst systems which are useful in the polymerization of olefin monomers in a manner analogous to that in current use with the aluminoxane compositions that are currently known and used in that manner.

The present invention is further exemplified by the Examples which follow.

until the entire charge of water had been added to the vial. This reaction can be exothermic and vigorous. Gas can be evolved. In many samples, solids formed. After the oxygenation was complete, the sample was allowed to settle, and the clear supernatant collected. The concentration of aluminum in the supernatant was assayed, and this result compared to the aluminum concentration calculated from aluminum charged and total sample mass. The aluminoxane product produced in each example was then evaluated in ethylene polymerizations with rac-ethylenebis-indenylzirconium dichloride at 85° C., an Al/Zr ratio of 1000, and an applied ethylene pressure of 150 psig. The reagents amounts and results are summarized in Tables 1 and 2.

TABLE 1

|  | TMAL (g) | DMAL-S (g) | toluene (g) | Water (g) | Water/Al mole/mole | O/Al mole/mole | soluble Al recovery (%) | soluble Al found (wt %) |
| --- | --- | --- | --- | --- | --- | --- | --- | --- |
| Comparative Example A | 5.0[1] | 0.0 | 45.1 | 0.62 | 0.51 | 0.51 | 80 | 2.9 |
| Comparative Example B | 5.0[1] | 0.0 | 45.0 | 1.00 | 0.81 | 0.81 | 54 | 2.0 |
| Example 1 | 2.5[2] | 5.6 | 45.3 | 0.97 | 0.76 | 1.26 | 47 | 1.7 |
| Example 2 | 2.5[2] | 5.6 | 45.0 | 0.61 | 0.48 | 0.98 | 72 | 2.6 |
| Example 3 | 2.4[2] | 5.1 | 45.5 | 0.36 | 0.30 | 0.80 | 93 | 3.1 |
| Example 4 | 0.8[2] | 2.5 | 25.5 | 0.15 | 0.30 | 0.90 | 91 | 2.3 |
| Example 5 | 2.5[2] | 2.5 | 45.1 | 0.42 | 0.47 | 0.80 | 81 | 2.2 |
| Example 6 | 1.8[2] | 2.5 | 30.9 | 0.29 | 0.39 | 0.79 | 86 | 2.7 |
| Example 7 | 0 | 10.9 | 48.3 | 0.60 | 0.46 | 1.46 | 100 | 3.3 |
| Example 8 | 0 | 10.8 | 48.3 | 0.95 | 0.74 | 1.74 | 100 | 3.3 |
| Example 9 | 0 | 5.0 | 22.8 | 0.06 | 0.10 | 1.10 | 100 | 3.2 |
| Example 10 | 0 | 3.9 | 23.2 | 0.12 | 0.25 | 1.25 | 100 | 2.6 |

[1]36.9 wt % Al.
[2]36.6 wt % Al.

EXAMPLES

Standard air-free glove box and Schlenk line techniques were used in these Examples. TMAL was provided by the Deer Park plant of Akzo Nobel Chemicals Inc. and contained 36.9 or 36.6 wt % Al. Dimethylaluminum trimethylsiloxide (DMAL-S) was prepared from dimethylaluminum chloride and sodium trimethylsiloxide, and sublimed before use. The DMAL-S was found to contain 17.75 wt % Al.

Comparative Example A, Examples 1–10

A series of trialkylaluminum compounds or mixtures of trialkylaluminum compounds were combined with solvent and charged to 130 mL glass serum capped vials. The solution of organoaluminum compounds was then cooled as required with a dry ice/isopropanol bath, and oxygenated by the slow dropwise addition of water. The water was added in small aliquots at reaction temperatures of from −50° to −25° C., with vigorous stirring, and the reaction allowed to warm to about 0° C. to permit complete reaction of each aliquot. This sequence of cooling and water addition was repeated

TABLE 2

| | TMAL (g) | DMAL-S (g) | O/Al mole/mole | DMAL-S/TMAL mole/mole | Supernate mass (g) | Soluble Al recovery (%) | Activity (kg PE/g Zr hr) |
|---|---|---|---|---|---|---|---|
| Comparative Example A | 5.0* | 0.0 | 0.51 | 0/1 | 30.1 | 47 | 390 |
| Comparative Example B | 5.0* | 0.0 | 0.81 | 0/1 | 26.5 | 29 | 590–640 |
| Example 1 | 2.5† | 5.6 | 1.26 | 1/1 | 29.5 | 26 | 0 |
| Example 2 | 2.5† | 5.6 | 0.98 | 1/1 | 35.2 | 48 | 530–590 |
| Example 3 | 2.4† | 5.1 | 0.80 | 1/1 | 40.3 | 70 | 390–430 |
| Example 4 | 0.8† | 2.5 | 0.90 | 3/2 | 24.4 | 73 | 380 |
| Example 5 | 2.5† | 2.5 | 0.80 | 2/1 | 39.5 | 64 | 570 |
| Example 6 | 1.8† | 2.5 | 0.79 | 2/3 | 30.6 | 75 | 660 |
| Example 7 | 0 | 10.9 | 1.46 | 1/0 | 57.6 | 98 | 0 |
| Example 8 | 0 | 10.8 | 1.74 | 1/0 | 57.0 | 98 | 0 |
| Example 9 | 0 | 5.0 | 1.10 | 1/0 | 27.8 | 100 | 0 |
| Example 10 | 0 | 3.9 | 1.25 | 1/0 | 27.1 | 100 | 0 |

\* = 36.9 wt % Al.
† = 36.6 wt % Al.

Examples 1 through 6 show that with proper choice of reagent amounts, an aluminoxane composition with the same activity as conventional PMAO can be prepared in much higher yield by the process of this invention.

The foregoing Examples, since they merely illustrate certain embodiments of the present invention, should not be construed in a limiting sense. The scope of protection sought is set forth in the claims which follow.

We claim:

1. A process for forming an aluminoxane composition comprising methylaluminoxane which comprises mixing trimethylaluminum, or a mixture of trimethylaluminum and one or more other trihydrocarbylaluminum compounds, with an organoaluminum compound containing a trialkylsiloxide moiety and then oxygenating the mixture to form the aluminoxane.

2. A process as claimed in claim 1 wherein the trialkylsiloxide moiety contained in the organoaluminum compound is of the formula —OSi(CH$_3$)$_3$.

3. A process as claimed in claim 1 wherein the organoaluminum compound containing the trialkylsiloxide moiety is of the formula (CH$_3$)$_2$AlOSi(CH$_3$)$_3$.

4. A process as claimed in claim 1 wherein the mole ratio basis on aluminum of trimethylaluminum to organoaluminum compound containing the trialkylsiloxide moiety ranges from about 1:10 to about 100:1.

5. A process as claimed in claim 2 wherein the mole ratio basis on aluminum of trimethylaluminum to organoaluminum compound containing the trialkylsiloxide moiety ranges from about 1:3 to about 5:1.

6. A process as claimed in claim 3 wherein the mole ratio basis on aluminum of trimethylaluminum to organoaluminum compound containing the trialkylsiloxide moiety ranges from about 1:2 to about 3:1.

7. A product formed by the process of claim 1.

8. A product formed by the process of claim 2.

9. A product formed by the process of claim 3.

10. A product formed by the process of claim 4.

11. A product formed by the process of claim 5.

12. A product formed by the process of claim 6.

13. The supported product formed by the process of claim 1.

14. The supported product formed by the process of claim 2.

15. The supported product formed by the process of claim 4.

16. The silica-supported product formed by the process of claim 1.

17. The silica-supported product formed by the process of claim 2.

18. The silica-supported product formed by the process of claim 4.

19. A catalyst composition for use in the polymerization of olefins which comprise the aluminoxane, optionally on a support, formed by the process of claim 1.

20. A catalyst composition for use in the polymerization of olefins which comprise the aluminoxane, optionally on a support, formed by the process of claim 2.

21. A catalyst composition for use in the polymerization of olefins which comprise the aluminoxane, optionally on a support, formed by the process of claim 4.

* * * * *